United States Patent [19]

Dye

[11] Patent Number: 4,822,926
[45] Date of Patent: Apr. 18, 1989

[54] ETHYLENE OXIDE/GLYCOLS RECOVERY PROCESS

[75] Inventor: Robert F. Dye, Sugar Land, Tex.

[73] Assignee: Shell Oil Company, Houston, Tex.

[21] Appl. No.: 161,875

[22] Filed: Feb. 29, 1988

[51] Int. Cl.$^4$ .................... C07C 29/00; C07C 29/80
[52] U.S. Cl. ................................ 568/867; 568/868; 568/613; 568/680; 568/621
[58] Field of Search ............... 568/867, 868, 613, 680, 568/621

[56] References Cited

U.S. PATENT DOCUMENTS

| 3,904,656 | 9/1975 | Broz | 568/867 |
| 3,970,711 | 7/1976 | Reiche et al. | 568/867 |
| 4,427,507 | 1/1984 | van Aken | 204/151 |

OTHER PUBLICATIONS

Freitas, E. R. et al., Shell's Higher Olefins Process, Chemical Engineering Progress, vol. 75, No. 1, pp. 73–76.

Primary Examiner—Howard T. Mars
Attorney, Agent, or Firm—Y. Grace Tsang

[57] ABSTRACT

A process for the recovery of a low concentration of ethylene oxide from an aqueous solution comprising salts, ethylene oxide and glycol which comprises the steps of:

(1) passing the aqueous solution comprising salts and ethylene oxide through a hydrolyzing zone at elevated temperature and elevated pressure for a sufficient length of time to insure the conversion of at least the greater portion of the ethylene oxide to glycols to obtain a dilute aqueous glycol solution;

(2) passing the dilute aqueous glycol solution through at least one flasher, wherein water is evaporated in the form of steam thereby producing at the bottom of the (last) flasher a solid-liquid two-phase slurry stream comprising salt-containing solids and a liquid phase comprising glycol, salt and water;

(3) sending said slurry-containing stream coming out of the (last) flasher to a centrifuge and centrifuging such stream to produce a solid phase and a liquid phase; and (4) passing said centrifuged liquid phase to a flasher wherein glycols are separated.

23 Claims, 1 Drawing Sheet

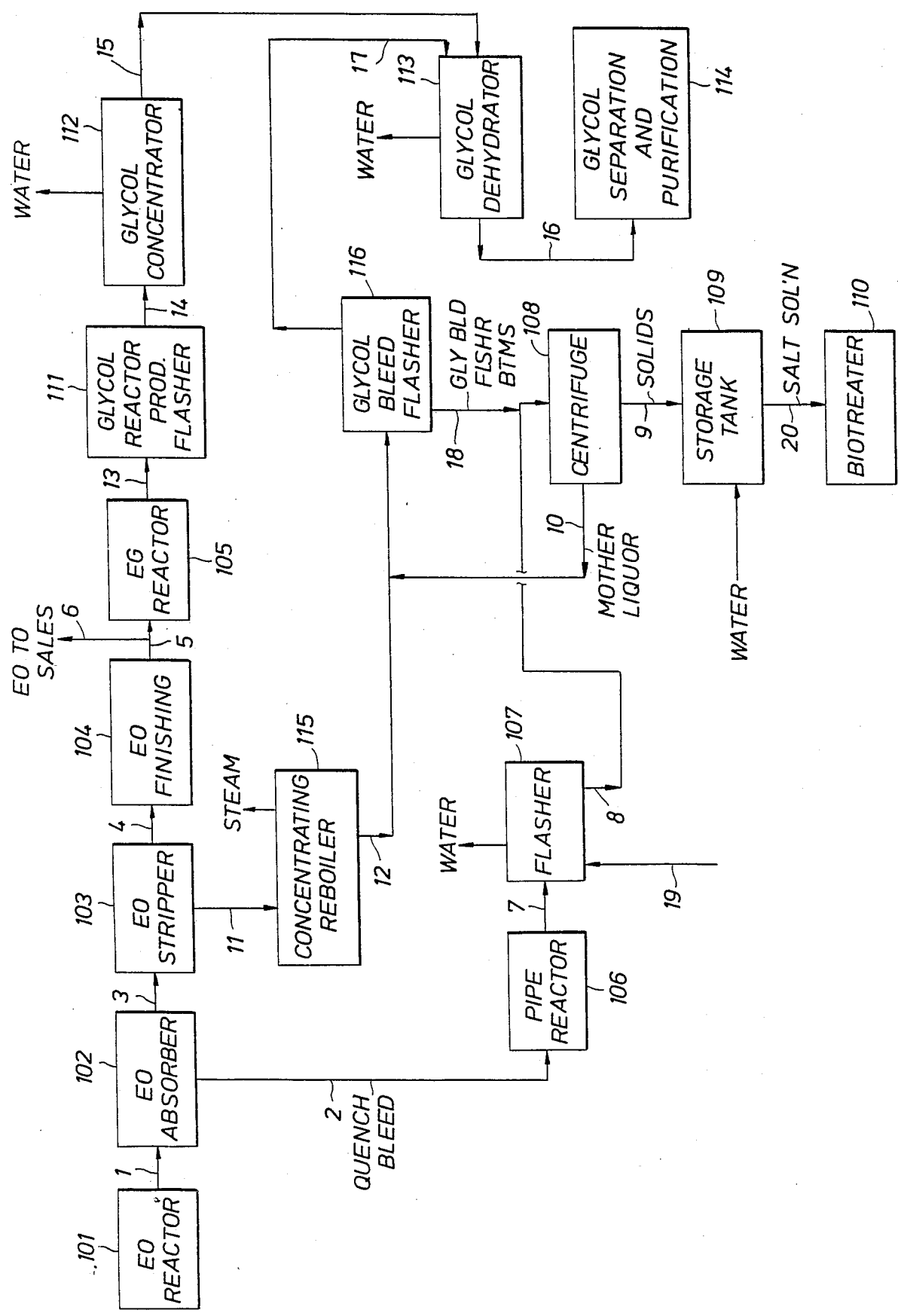

– 4,822,926 –

ETHYLENE OXIDE/GLYCOLS RECOVERY PROCESS

FIELD OF THE INVENTION

The present invention relates to an improved ethylene oxide process whereby a low concentration of ethylene oxide in a quench bleed is recovered as glycols. The present invention also relates to a process for the recovery of a low concentration of glycols from a salt-containing aqueous stream.

BACKGROUND OF THE INVENTION

In some conventional ethylene oxide plants, the aqueous quench bleed from the quench section of the ethylene oxide absorber is sent directly to a disposal well. The quench bleed contains a low concentration of ethylene oxide. Ethylene oxide (EO) has been shown to be mutagenic to test animals and is a "suspected carcinogen." EO in pure form has a very low flash point and is highly flammable. The Threshold Limit Value (TLV) for EO based on the standards set by the American Conference of Governmental Industrial Hygienists is 1 ppm in air. To avoid the contamination of water supply with EO, the Environmental Protection Agency has ordered that the disposal of the ethylene oxide to the well be discontinued. A method for removal of ethylene oxide from the aqueous quench bleed is therefore definitely needed.

One method for accomplishing such ethylene oxide removal has been discussed in U.S. Pat. No. 4,427,507, issued Jan. 24, 1984, which teaches a process for separating glycols from an electrolyte-containing aqueous solution which can be a quench bleed from an ethylene oxide plant. The process comprises electrolyzing said solution to increase the glycol to electrolyte content and subsequently removing a substantial part of the water. Ethylene oxide is removed by distillation.

It is an object of the present invention to provide a process enabling the conversion of a low concentration of ethylene oxide in a salt-containing aqueous quench bleed to glycols which are considered much less toxic than EO. Glycols, in general, have much higher flash points and are not flammable. The glycols produced can be recovered. In a typical ethylene oxide plant, as much as 24,000 lbs. of glycols per day can be recovered from the quench bleed which amounts to about six thousand dollars worth of glycols products.

A further object of the invention is the provision of an improved process enabling the efficient recovery of a low concentration of ethylene glycol from a salt-containing aqueous solution.

Still another object of the invention is to provide a process for the recovery of glycols from the bottoms stream of the glycol bleed flasher in an ethylene glycol plant. The glycols from the bottoms stream of the glycol bleed flasher are normally disposed as a waste stream in a conventional plant. The overall yield of the EO/EG process is increased using this process contemplated by the present invention.

Other objects and advantages of the present invention will become apparent from the following detailed description thereof, made with reference to the attached drawing wherein the single FIGURE represents one form of apparatus capable of being used in carrying out the process of the invention.

SUMMARY OF THE INVENTION

The present invention provides a process for the recovery of a low concentration of ethylene oxide from an aqueous solution comprising salts and ethylene oxide which comprises the steps of:

(1) passing the aqueous solution comprising salts and ethylene oxide through a hydrolyzing zone at elevated temperature and elevated pressure for a sufficient length of time to insure the conversion of at least the greater portion of the ethylene oxide to glycols to obtain a dilute aqueous glycol solution;

(2) passing the dilute aqueous glycol solution through at least one flasher, wherein water is evaporated in the form of steam thereby producing at the bottom of the (last) flasher a solid-liquid two-phase slurry stream comprising salt-containing solids and a liquid phase comprising glycol, salt and water;

(3) passing said slurry-containing stream coming out of the (last) flasher to a centrifuge and centrifuging such stream to produce a solid phase and a liquid phase; and (4) passing said centrifuged liquid phase to a glycol bleed flasher wherein glycols are separated and recovered.

The present invention also provides a process for the recovery of a low concentration of glycols from a salt-containing aqueous solution which comprises the steps of passing the aquous solution to the flasher(s) as described in step (2) of the above-mentioned process and continuing the process by following step (3) and step (4).

In another aspect of the present invention, a process is provided for the recovery of glycols from the salt-containing glycol mixture from the bottom of the glycol bleed flasher in an ethylene glycol plant. The process comprises the recycling of said bottoms from the glycol bleed flasher to the above-mentioned centrifuge to be centrifuged in combination with the slurry stream coming out of the flasher.

The present invention provides a method for obviating the environmental protection problem and achieving an economic benefit by converting ethylene oxide in the glycol bleed to glycols and recovering the glycols as additional products.

BRIEF DESCRIPTION OF THE DRAWING

The appended drawing is a schematic flow diagram of an EO quench bleed recovery system in conjunction with a glycol recovery system in an EO/EG plant.

A detailed description of the process illustrated by the drawing can be found in the detailed description hereinafter.

Throughout the drawing, the same reference numerals have been used for similar purposes, and accessories such as valves, pumps and control instruments not necessary for the purpose of understanding the present invention are not (all) shown.

DETAILED DESCRIPTION OF THE INVENTION

Referring to the appended drawing, the ethylene oxide (EO) reactor 101 is constructed as a large, fixed-tubesheet heat exchanger containing several thousand reactor tubes filled with EO catalyst. Suitable catalysts include alumina-supported silver catalysts. Ethylene is reacted with oxygen over the catalyst to form EO. Some of the EO formed may isomerize to acetaldehyde (ACH) which, in turn, is rapidly oxidized to carbon dioxide and water, so that only traces of ACH are found in the reactor product. Carbon dioxide and water are also formed in an ethylene oxidation competing with the main reaction. This reaction is suppressed by the use of a chlorine-containing catalyst moderator.

The reactor product gaseous stream 1 typically comprises methane, ethylene, oxygen, carbon dioxide, water, EO, ACH, formaldehyde, acidic components such as acetic acid, formic acid, etc. Said stream passes through heat exchangers (not shown), wherein heat is removed, and is then sent to the quench section of an EO absorber 102 wherein it is scrubbed with a cooled recirculating slightly alkaline aqueous quench stream to absorb and neutralize acidic compounds such as acetic acid, formic acid, etc. (Traces of formaldehyde formed in the EO reactor are partially removed here.) This neutralization is maintained by the continuous addition of a caustic solution, which is typically an aqueous solution containing from about 10.0 wt. % to about 30 wt. % of sodium hydroxide, to the recirculating aqueous quench stream. The carbon dioxide dissolved in the quench stream reacts with the added caustic to form sodium carbonate and sodium bicarbonate, the predominant salts formed. Water formed in the EO reactor from side reaction is partially condensed and accumulates in the quench stream. Excess liquid is drained as the "quench bleed" 2 to satisfy material balance requirements.

The gases from the quench (or lower) section of the EO absorber passes through a trap-out tray into the main portion of the EO absorber where they are scrubbed with water at about 60° F. to 95° F. to recover EO. The stream 3 with the major portion of the product EO absorbed therein is sent to an EO stripper 103 whereby the majority of the ethylene oxide is steam stripped and leaves the top of the stripper. This tops stream 4 typically contains from about 45 wt. % to about 55 wt. % of ethylene oxide, from about 40 wt. % to about 50 wt. % of water, and from about 1.0 wt. % to about 4.0 wt. % of carbon dioxide, and smaller concentrations of ethylene and oxygen. This stream is subjected to ethylene oxide finishing processes 104. The finished ethylene oxide 5 is sent to an ethylene glycol reactor 105 in an ethylene glycol plant to be converted into glycols and/or is sold as commercial EO product 6.

The glycols referred to hereinafter are difunctional alcohols of the aliphatic series, e.g., aliphatic compounds containing two hydroxyl groups, which include, but not limited to, monoethylene glycol, diethylene glycol, triethylene glycol, tetra-ethylene glycol, etc.

The quench bleed 2 which contains typically from about 0.5 wt. % to about 3.0 wt. % of ethylene oxide, from about 0.5 wt. % to about 3.5 wt. % of glycols, from about 0.5 wt. % to about 3.0 wt. % of salts comprising sodium carbonate and/or sodium bicarbonate, from about 90 wt. % to 98.5 wt. % of water and optionally small quantities, for example less than 1.0 wt. %, of other chemicals, for example, acetaldehyde, formaldehyde, sodium acetate, sodium formate, etc. In some conventional plants, the quench bleeds are sent to disposal wells. The quench bleed contains a low concentration of ethylene oxide. Ethylene oxide (EO) has been shown to be mutagenic to test animals and is a "suspected carcinogen." EO in pure form has a very low flash point and is highly flammable. The Threshold Limit Value (TLV) for EO based on the standards set by the American Conference of Governmental Industrial Hygienists is 1 ppm in air. To avoid the contamination of water supply with EO, the Environmental Protection Agency has ordered that the disposal of the ethylene oxide to the wells be discontinued. A different method for handling this quench bleed is definitely needed and is provided by the instant invention.

In the instant invention, the quench bleed 2 is pumped via a high-head pump (not shown), at an elevated pressure, through preheaters into a hydrolyzing zone 106 to produce total (typically 99.99%) hydrolysis of the EO content into glycols. The hydrolyzing zone 106 may comprise a chamber or can suitably be a pipe reactor. The maintenance of a temperature in the hydrolyzing zone 10 in the range of, for example, from about 325° F. to about 450° F., and preferably from about 330° F. to about 385° F. is satisfactory. Pressures within the chamber or pipe reactor is preferably maintained in the range of, for example, from about 350 psig to about 500 psig. The time of residence of the quench bleed in the hydrolyzing zone 106 will vary in accordance with the specific temperature and pressure maintained in the hydrolyzing zone. In general, a time less than 60 minutes is sufficient to obtain a conversion of at least a substantial part of the ethylene oxide to glycols. A residence time in the hydrolyzing zone in the range of, for example, from about one minute to about 30 minutes is satisfactory. A longer residence time in the hydrolyzing zone, however, when resorted to is to be considered within the scope of the invention. The elevated pressure is needed to avoid the separation of the quench bleed into two phases and thereby keeping ethylene oxide in the aqueous solution. Pipe reactors which are from about 2 to about 15 in. in diameter and from about 5 to about 100 ft. in length are suitable. The benefit of using a pipe reactor is that it provides suitable residence time and also provides less back mixing of the reaction mixture thereby avoiding excessive formation of diethylene glycol (DEG) and triethylene glycol (TEG) and heavier glycols, thus producing higher percentage of monoethylene glycol (MEG).

The hydrolyzed stream 7 from the hydrolyzing zone 106, for example the pipe reactor, is passed to at least one flasher 107, typically, but not limited to, a two-stage refluxed flash system, for water removal. In a preferred embodiment, a two-stage refluxed flash system is used. A refluxed flasher operates such that water is evaporated in the form of steam and leaves from the top of the flasher essentially glycol-free, while trays effect a concentration of glycols and salts at the bottom. The mixture leaving the bottom of the first flasher is passed to the second flasher for another cycle of the water-removal process. The steam produced from the top of the first-stage flasher may serve as the motive energy for the second-stage flasher.

The maintenance of a temperature, for example, in the range of from about 250° F. to about 310° F. and a pressure, for example, in the range of from about 30 psig to about 40 psig in the first flasher is satisfactory. The maintenance of a temperature at the bottom of the last flasher, for example, in the range of from about 220° F. to about 280° F. and a pressure at the bottom of the last flasher, for example, in the range of from about 1.5 psig to about 3.0 psig is satisfactory. The intermediate flasher(s), if present, will have intermediate temperature(s) and pressure(s) between the first flasher and the last flasher. The bottoms stream 8 of the last flasher is a two-phase stream typically containing from about 8.0 wt. % to about 17.0 wt. % suspended solids, from about 50.0 wt. % to about 70.0 wt. % of glycols and from about 15.0 wt. % water to about 30.0 wt. % water. The liquid phase contains water, glycol and typically from about 1.0 wt. % to about 10.0 wt. % of sodium carbonate and/or sodium bicarbonate in solution. The glycol content of the steam coming out of the top of the flashers is typically from about 0.001 wt. % to about 0.1 wt. %. The steam generated from the first flasher is, for example, from about 15 psig to about 65 psig and from about 250° F. to about 310° F. and that from the last flasher is, for example, from 180° F. to about 250° F. and from about 0.3 psig to about 1.5 psig. The steam can be utilized as heat source for the EO/EG plant.

The stream 8 exiting at the bottom of the last stage flasher is sent to a centrifuge 108 wherein a salt cake 9 is dropped out, redissolved with water in a storage tank 109 and sent to a biotreater 110 and to be disposed thereafter. The salt cake 9 contains, for example, from about 1.0 wt. % to about 10.0 wt. % water, from about 2.0 wt. % to about 20.0 wt. % of glycols and from about 70.0 wt. % to about 97.0 wt. % of salts comprising sodium carbonate and/or sodium bicarbonate.

The mother liquor 10 from the centrifugation process contains typically from about 1.0 wt. % to about 5.0 wt. % sodium carbonate and/or sodium bicarbonate, from about 40.0 wt. % to about 60.0 wt. % water and from about 40.0 wt. % to about 60 wt. % of glycols. This stream 10 is subject to glycols purification and recovery processes whereby glycols are recovered as finished and products.

Many EO plants are connected to EG plants. A portion of the EO-containing tops stream 4 leaving the EO stripper 103, after being finished by a series of finishing processes 104, can be sent to a EG reactor 105 in the EG plant to be hydrolyzed into glycols. The glycol-containing stream is separated and purified via the glycol reactor product flasher 111, glycol concentrator 112, glycol dehydrator 113 and other separation and purification devices 114 to produce glycol finished end-products. The glycol reactor product flasher, glycol concentrator, and dehydrator are all refluxed tray columns which reject water as steam tops products, essentially glycol-free, at the same time concentrating glycols as bottoms products.

The bottoms stream 11 of the EO stripper 103 is normally sent to a concentrating reboiler 115 wherein water in the form of steam is removed and the bottoms stream 12 is sent to the glycol bleed flasher 116 in the EG plant. The above-mentioned mother liquor stream 10 from the centrifuge 108 can be sent to the glycol bleed flasher 116 to be combined with stream 12. In the glycol bleed flasher 116, water and glycols are evaporated. The overhead stream 17, which contains, for example, from about 10.0 wt. % of to about 30 wt. % of glycols and from about 65.0 wt. % to about 90.0 wt. % water, is sent to the glycol dehydrator 113. The maintenance of a temperature, for example, in the range of from about 200° F. to about 275° F. and a pressure, for example, in the range of from about 120 mm Hg to about 200 mm Hg in the glycol bleed flasher is satisfactory.

In the glycol dehydrator 113, water is removed from the top of the dehydrator while trays in the dehydrator hold back glycols. The dehydrator is a vacuum column which effects the final dehydration of the glycols prior to separation and purification as glycol end-products. The temperature at the top of the dehydrator is, for example, from about 100° F. to about 125° F. and that at the bottom of the dehydrator is, for example, from about 250° F. to about 350° F. The pressure at the top of the dehydrator is, for example, from about 60 mm Hg to about 100 mm Hg and that at the bottom is, for example, from about 110 mm Hg to about 160 mm Hg. The bottoms 16 which contain, for example, from about 70.0 wt. % to about 90.0 wt. % of mono-ethylene glycol, from about 10 wt. % to about 25 wt. % of di-ethylene glycol, and from about 0.5 wt. % to about 3.5 wt. % of triethylene glycol are subjected to a series of glycol separation and purification processes 114 and glycols are recovered as products.

In the second embodiment of the present invention, glycols in an aqueous stream 7 or 19, either originating in the EO plant scheme shown or originating in a non-EO plant operation, containing a low concentration of glycols and salts, for example sodium chloride, sodium bicarbonate and/or sodium carbonate can be recovered by subjecting the stream to the flashing process in the flasher(s) 107 and following the subsequent process steps as described above. The aqueous glycol stream contains, for example, from about about 0.5 wt. % to about 10.0 wt. % of glycols, from about 0.1 wt. % to about 10.0 wt. % of salts, for example sodium carbonate and/or sodium bicarbonate.

The process according to the second embodiment of the invention is particularly suitable for use in recovering glycols from the hydrolyzed quench bleed in an ethylene oxide plant as described above.

Another use of the second embodiment of the invention is found in the dewatering of natural gas by using glycol, for instance immediately after winning, being produced, or during transport through pipelines. When gas is produced at a reservoir, water, and hence also some dissolved salt—mainly NaCl—becomes entrained. The gas is then dried by absorption in a glycol, notably triethylene glycol. In the subsequent regeneration of this glycol—for instance in a vacuum regenerator—salt deposits cause problems. These problems may be overcome by treating the glycol-water mixture according to the second embodiment of the invention, and thus separating salts from glycols and water which can then be reused in the dewatering of natural gas.

As a third option for use the application also relates to a process for the preparation of $C_{10}$–$C_{20}$ alpha-olefins by way of oligomerization of ethene using a catalyst dissolved in butane-diol, characterized in that salt-contaminated butanediol is worked up to be recirculated using the process according to the invention. A further description of this process for the preparation of olefins may be found in the article published by E. R. Freitas and C. R. Gum in *Chemical Engineering Progress* (Jan. 1979), pp. 73–76.

Finally, another use of the second embodiment of the present invention is found in the regeneration of glycol-water antifreeze mixtures, for instance for motor car engines.

In the third embodiment of the present invention, the bottoms 18 from the glycol bleed flasher can be recycled back to the centrifuge 108 to be combined with the bottoms from the flasher(s) 107 and subject to the subsequent separation and recovery processes as described above. The bottoms 18 contains, for example, from about 30.0 wt. % to about 70.0 wt. % of salts and from about 30.0 wt. % to about 70 wt. % of glycols, and water. Additional glycols can be recovered as products accordingly.

The ranges, limitations and steps provided in the instant specification and claims are those which are believed to particularly point out and distinctly claim the instant invention. It is, however, understood that other ranges, limitations and the use of additional steps that perform substantially the same function in substantially the same manner to obtain the same or substantially the same result are intended to be within the scope of the instant invention as defined by the instant specification and claims.

What is claimed is:

1. A process for recovery of a low concentration of ethylene oxide as glycols from an aqueous solution comprising salts and ethylene oxide, which comprises the steps of:
   (1) passing the aqueous solution comprising salts and ethylene oxide through a hydrolyzing zone at elevated temperature and elevated pressure for a sufficient length of time to insure the conversion of at least the greater portion of the ethylene oxide to glycols to obtain a dilute aqueous glycol solution;
   (2) passing the dilute aqueous glycol solution through at least one flasher, wherein water is evaporated in the form of steam thereby producing at the bottom of the (last) flasher a solid-liquid two-phase slurry stream comprising salt-containing solids and a liquid phase comprising glycol, salt and water;
   (3) sending said slurry-containing stream coming out of the (last) flasher to a centrifuge and centrifuging such stream to produce a solid phase and a liquid phase; and
   (4) passing said centrifuged liquid phase to a glycol flasher wherein glycols are separated.

2. The process as claimed in claim 1, wherein said aqueous solution comprising salts and ethylene oxide comprises water, from about 0.5 to about 3.0 wt. % of ethylene oxide, and from about 0.5 to about 3.0 wt. % of salts selected from the group consisting of sodium carbonate, sodium bicarbonate and a mixture thereof.

3. The process as claimed in claim 2, wherein at least about 99.0 wt. % of the ethylene oxide is converted to glycols in said hydrolyzing zone.

4. The process as claimed in claim 1, wherein said hydrolyzing zone comprises a pipe reactor.

5. A process for recovery of a low concentration of ethylene oxide as glycols from a quench bleed from a quench section of an ethylene oxide absorber in an ethylene oxide plant, said quench bleed comprising water, ethylene oxide, glycols, and salts; which process comprises the steps of:
   (1) passing the ethylene oxide and salt-containing quench bleed through a hydrolyzing zone at elevated temperature and elevated pressure for a sufficient length of time to insure the conversion of at least the greater portion of the ethylene oxide to glycols to produce a dilute glycol-containing aqueous solution;
   (2) passing the dilute glycol-containing solution through at least one flasher, wherein water is evaporated in the form of steam thereby obtaining at the bottom of the (last) flasher a solid-liquid two-phase slurry stream comprising salt-containing solids and a liquid phase comprising glycols, salts and water;
   (3) sending said slurry-containing stream coming out of the (last) flasher to a centrifuge and centrifuging such stream to produce a solid phase and a liquid phase; and
   (4) passing said centrifuged liquid phase to a glycol flasher whereby glycols are separated.

6. The process as claimed in claim 5, wherein said hydrolyzing zone comprises a pipe reactor.

7. The process as claimed in claim 5, wherein said quench bleed comprises from about 0.5 to about 3.0 wt. % of ethylene oxide, from about 0.5 to about 3.0 wt. % glycols, from about 0.5 to about 3.0 wt. % of salts selected from the group consisting of sodium carbonate, sodium bicarbonate and a mixture thereof, and from about 90.0 wt. % to 98.5 wt. % of water.

8. The process as claimed in claim 6, wherein said pipe reactor is from about 2 to about 15 in. in diameter, from about 5 to about 100 ft. in length; wherein the temperature in the pipe reactor is from about 325° F. to about 450° F. and the pressure therein is from about 350 psig to about 500 psig.

9. The process as claimed in claim 7, wherein at least about 99.0 wt. % of the ethylene oxide is converted to glycols after passing through the hydrolyzing zone.

10. The process as claimed in claim 7, wherein said hydrolyzing zone is a pipe reactor and at least about 99.0 wt. % of the ethylene oxide is converted to glycols after passing through said pipe reactor.

11. The process as claimed in claim 5, wherein said two-phase slurry stream from the bottom of the (last) flasher comprises from about 15.0 to about 30.0 wt. % water, from about 50.0 to about 70.0 wt. % glycols, and from about 10.0 to about 20.0 wt. % salts selected from the group consisting of sodium bicarbonate, sodium carbonate and a mixture thereof.

12. The process as claimed in claim 11, wherein said centrifuged liquid phase comprises from about 40.0 wt. % to about 60.0 wt. % of water, from about 40.0 wt. % to about 60.0 wt. % of glycols, and from about 1.0 wt. % to about 10.0 wt. % of salts selected from the group consisting of sodium carbonate, sodium bicarbonate and mixture thereof.

13. The process as claimed in claim 12, wherein said centrifuged solid phase is a salt cake comprising from about 70.0 wt. % to about 97.0 wt. % of salts selected from the group consisting of sodium carbonate, sodium bicarbonate and mixture thereof, from about 2.0 wt. % to about 20.0 wt. % of glycols, and from about 1.0 to about 10.0 wt. % of water.

14. A process for the recovery of ethylene oxide as glycols from a quench bleed stream from a quench section of an ethylene oxide absorber in an ethylene oxide plant, said quench bleed comprising from about 0.5 wt. % to about 3.0 wt. % of ethylene oxide, from about 0.5 to about 3.5 wt. % of glycols, from about 0.5 to about 3.0 wt. % of salts selected from the group consisting of sodium carbonate, sodium bicarbonate and a mixture thereof, and from about 90.0 wt. % to about 98.5 wt. % of water, which process comprises the steps of:
   (1) passing the ethylene oxide-containing quench bleed through a pipe reactor at from about 325° F. to about 450° F. and from about 350 psig to about 500 psig for a sufficient length of time to insure the conversion of at least 99% of the ethylene oxide to glycols to produce a dilute aqueous glycol solution comprising from about 1.5 wt. % to about 6.5 wt. % of glycols, from about 0.5 wt. % to about 3.0 wt. % salts, from 90.0 wt. % to about 98.0 wt. % water, and less than 0.01 wt. % of ethylene oxide;
   (2) subjecting the dilute aqueous glycol solution to multi-stage evaporation, whereby water is evaporated in the form of steam thereby obtaining at the last stage a solid-liquid two-phase slurry stream comprising from about 15.0 to about 30.0 wt. % water, from about 50.0 to about 70.0 wt. % glycols, and from about 10.0 to about 20.0 wt. % salts selected from the group consisting of sodium bicarbonate, sodium carbonate and a mixture thereof;

(3) sending said slurry-containing stream from the last stage of the multi-stage evaporation unit to a centrifuge and centrifuging such stream to produce a solid phase and a liquid phase, (4) passing said centrifuged liquid phase comprising from about 40.0 wt. % to about 60.0 wt. % of water, from about 40.0 wt. % to about 60.0 wt. % of glycols, and from about 1.0 wt. % to about 10.0 wt. % of salts selected from the group consisting of sodium carbonate, sodium bicarbonate and mixture thereof to a glycol flasher, wherein the majority of glycols are evaporated as a vapor stream and sent to a glycol dehydrator whereby glycols are separated; and (5) redissolving said solid-phase, which is a salt cake comprising from about 80.0 wt. % to about 90.0 wt. % of salts selected from the group consisting of sodium carbonate, sodium bicarbonate, and mixture thereof, from about 5.0 wt. % to about 15.0 wt. % of glycols, and from about 1.0 to about 8.0 wt. % of water in an aqueous solution to obtain a salt containing-solution comprising from about 0.1 wt. % to about 40.0 wt. % of salts selected from the group consisting of sodium carbonate, sodium bicarbonate, and a mixture thereof, from about 0.01 wt. % to about 5.0 wt. % of glycols, and from about 60.0 wt. % to about 99.9 wt. % of water.

15. A process for recovery of low concentration of glycols from glycols and salt-containing aqueous solution which comprises the steps of:

(1) passing said aqueous solution through at least one flasher, whereby water is evaporated in the form of steam thereby obtaining at the bottom of the (last) flasher a solid-liquid two-phase slurry-containing stream comprising salt-containing solids and a liquid phase comprising glycols, salts and water;

(2) sending said slurry-containing stream to a centrifuge and centrifuging said stream to produce a solid phase and a liquid phase; and (3) passing said centrifuged liquid phase to a glycol flasher wherein glycols are separated.

16. The process as claimed in claim 15, wherein said two-phase slurry-containing stream comprises from about 15.0 to about 30.0 wt. % water, from about 50.0 to about 70.0 wt. % glycols, and from about 10.0 to about 20.0 wt. % salts selected from the group consisting of sodium bicarbonate, sodium carbonate, and a mixture thereof.

17. The process as claimed in claim 15, wherein said liquid phase from said centrifuge comprises from about 40.0 wt. % to about 60.0 wt. % of water, from about 40.0 wt. % to about 60.0 wt. % of glycols, and from about 1.0 wt. % to about 10.0 wt. % of salts selected from the group consisting of sodium carbonate, sodium bicarbonate, and mixture thereof.

18. The process as claimed in claim 15, wherein said solid phase from the centrifuge is a salt cake comprising from about 70.0 wt. % to about 97.0 wt. % of salts selected from the group consisting of sodium carbonate, sodium bicarbonate, and a mixture thereof, from about 2.0 wt. % to about 20.0 wt. % of glycols, and from about 1.0 to about 10.0 wt. % of water.

19. A process for the recovery of glycols from a dilute aqueous glycol solution comprising from about 1.5 wt. % to about 6.5 wt. % of glycols, from about 0.5 wt. % to about 3.0 wt. % salts, from 90.0 wt. % to about 98.0 wt. % water, and less than 0.01 wt. % of ethylene oxide, which process comprises the steps of:

(1) subjecting the dilute aqueous glycol solution to multi-stage evaporation, whereby water is evaporated in the form of steam thereby obtaining at the last stage a solid-liquid two-phase slurry-containing stream comprising from about 15.0 to about 30.0 wt. % water, from about 50.0 to about 70.0 wt. % glycols, and from about 10.0 to about 20.0 wt. % salts selected from the group consisting of sodium bicarbonate, sodium carbonate, and a mixture thereof.

(2) sending said slurry-containing stream to a centrifuge and centrifuging such stream to produce a solid phase and a liquid phase are produced;

(3) passing said liquid phase comprises from about 40.0 wt. % to about 60.0 wt. % of water, from about 40.0 wt. % to about 60.0 wt. % of glycols, and from about 1.0 wt. % to about 10.0 wt. % of salts selected from the group consisting of sodium bicarbonate, sodium carbonate, and mixture thereof to a glycol bleed flasher in an ethylene glycol plant downstream from an ethylene oxide plant, wherein the majority of glycols are evaporated as a vapor stream and sent to a glycol dehydrator whereby the glycols are separated;

(4) redissolving said solid phase, which is a salt cake comprising from about 80.0 wt. % to about 90.0 wt. % of salts selected from the group consisting of sodium carbonate, sodium bicarbonate, and mixture thereof, from about 5.0 wt. % to about 15.0 wt. % of glycols, and from about 1.0 to about 8.0 wt. % of water, in an aqueous solution to obtain a salt containing-solution comprising from about 0.1 wt. % to about 40.0 wt. % of salts selected from the group consisting of sodium carbonate, sodium bicarbonate, and a mixture thereof, from about 0.01 wt. % to about 5.0 wt. % of glycols, and from about 60.0 wt. % to about 99.9 wt. % of water.

20. The process as claimed in claim 5, wherein said centrifuged liquid phase is passed to a glycol bleed flasher in an ethylene glycol plant downstream from an ethylene oxide plant, wherein a major amount of the glycols are evaporated as a vapor stream and sent to a glycol dehydrator to be separated; wherein bottoms from the glycol bleed flasher is recycled to the centrifuge in step (3) to be centrifuged in combination with said slurry coming out of the (last) flasher in step (2).

21. The process as claimed in claim 14, wherein said centrifuged liquid phase is passed to a glycol bleed flasher in an ethylene glycol plant downstream from an ethylene oxide plant, wherein a major amount of the glycols are evaporated as a vapor stream and sent to a glycol dehydrator to be separated and recovered; wherein bottoms from the glycol bleed flasher, comprising water, from about 30.0 wt. % to about 70.0 wt. % of said salts and from about 30.0 wt. % to 70.0 wt. % of glycols, is recycled to the centrifuge in step (3) to be centrifuged in combination with said slurry coming out of the multi-stage evaporator in step (2).

22. The process as claimed in claim 15, wherein said centrifuged liquid phase is passed to a glycol bleed flasher in an ethylene glycol plant downstream from an ethylene oxide plant, wherein a major amount of the glycols are evaporated as a vapor stream and sent to a glycol dehydrator to be separated and recovered; wherein bottoms from the glycol bleed flasher is recycled to the centrifuge in step (2) to be centrifuged in combination with said slurry from the (last) flasher in step (1).

23. The process as claimed in claim 19, wherein said centrifuged liquid phase is passed to a glycol bleed flasher in an ethylene glycol plant downstream from an ethylene oxide plant, wherein a major amount of the glycols are evaporated as a vapor stream and sent to a glycol dehydrator to be separated and recovered; wherein bottoms from the glycol bleed flasher, comprising water, from about 35 wt. % to about 65 wt. % of said salts and from about 35 wt. % to 65 wt. % of glycols, is recycled to the centrifuge in step (2) to be centrifuged in combination with said slurry coming out of the multi-stage evaporator in step (1).

* * * * *